United States Patent [19]

Welsh

[11] 4,050,911
[45] Sept. 27, 1977

[54] GAS CHROMATOGRAPH OVEN

[75] Inventor: Paul Bryce Welsh, Wilmington, Del.

[73] Assignee: Hewlett-Packard Company, Palo Alto, Calif.

[21] Appl. No.: 582,053

[22] Filed: May 29, 1975

Related U.S. Application Data

[63] Continuation of Ser. No. 499,894, Aug. 23, 1974, abandoned.

[51] Int. Cl.$^2$ ............................................. B01D 15/08
[52] U.S. Cl. ........................................ 55/197; 55/386; 432/199
[58] Field of Search .................... 55/67, 197, 386, 267; 210/198 C; 165/12, 13, 75; 219/391, 403, 404; 432/199, 200, 201, 42

[56] References Cited

U.S. PATENT DOCUMENTS 2,963,898  12/1960  Reynolds et al. ....................... 55/386
3,419,255  12/1968  Carel et al. ...................... 432/199 X Primary Examiner—John Adee
Attorney, Agent, or Firm—Allston L. Jones; Stephen P. Fox

[57] ABSTRACT

A method for cooling gas chromatograph ovens with ambient room temperature air utilizing two separate air passages through an oven door. The door remains closed during the heating and cooling cycles which take place inside the oven housing. A rotating stirring fan internal to the oven creates regions of relatively higher and lower air pressures. The two air passages are disposed adjacent to these pressure regions to draw room temperature air into the oven, and to exhaust hot air from the oven. Within the oven door there is a movable, spring mounted, oven closure hatch in which the first air passage is located. This air passage is opened and closed by a movable cover. The hatch also establishes the second air passage when it is spaced-apart from the oven housing. Both air passages are opened and closed in response to movement of the hatch. An actuation device that can interface with a programmable actuation controller opens and closes the hatch as necessary for cooling the inside of the oven housing.

9 Claims, 5 Drawing Figures

GAS CHROMATOGRAPH OVEN

CROSS REFERENCE TO RELATED APPLICATION

This is a continuation of application Ser. No. 499,894, filed Aug. 23, 1974, now abandoned.

BACKGROUND OF THE INVENTION

This invention is concerned generally with gas chromatography, and more particularly with the oven that contains the separating colomns in a gas chromatograph system.

A gas chromatograph oven usually comprises a thermally insulated housing internally accessable through a door, a heating element, and a motor driven fan for stirring the air in the housing. The stirring fan continuously mixes the air within the oven to minimize temperature gradients which could adversely affect the performance of the chemical process within the separating columns.

An important requirement of a gas chromatograph oven is that it be capable of rapid cooling from a higher temperature to a closely maintained lower temperature. Typically this has been accomplished by either opening the oven door to permit the interior air to be cooled by the ambient room temperature air, or by cryoinjection of a coolant such as liquid $CO_2$ or $N_2$ into the oven. These methods, as presently utilized, have several disadvantages.

To utilize the ambient room temperature air for cooling, the door must be set ajar either manually or automatically. A preprogrammed control mechanism is used to open and close the door as necessary in the automatic mode. Sometimes, an auxilary blower is used to aid in mixing the cooler ambient room temperature air with the warmer air within the oven. When the oven door is opened partially, a turbulent air region is created around this opening by the interaction of the hot air which tries to escape from the oven and the room temperature air which tries to replace the hot air. The result is undesirably large temperature variations with time and from point to point in the chromatographic separation column area of the oven. These temperature variations are detrimental to the reproducibility of chromatographic separations, hence chromatographic separations should not be carried out with the door ajar. Necessitating that the oven door be closed results in two disadvantages. First, the closed oven temperature will stabilize typically no lower than 25° C above ambient room temperature without power applied to the oven heater. The elevated oven temperature is generated by friction between the rotating stirring fan and the circulating air within the oven. Additional oven heat is supplied by auxiliary heated devices, e.g. the independently heated cryoinjection mechanism. At temperatures between ambient and 25° C above ambient chromatographic separations cannot typically be carried out without the use of cryogenic coolants. Second, the heat retained by the walls of the oven necessitate the cooling of the oven air far below the new control temperature range before the door is closed. The additional cooling is necessary since the heat stored in the walls of the oven can raise the oven temperature considerably. Thus, the time between chromatographic separations is much longer than would be required to cool the oven air from the higher temperature to the lower temperature.

Sometimes the rate of cooling of the oven is improved by the use of an auxiliary blower, but the use of such an additional component is undesirable because of the additional cost and maintenance potential. The open, or opening oven door also presents a safety hazard to the operator since under preprogrammed control the door may open unexpectedly, and when open it may present an obstacle to the free movement of the operator, as well as exposing him to potentially hot interior oven surfaces on the order of 200° C, for example.

The use of coolants injected into the oven for cooling the internal air to near ambient temperatures (between ambient and about 25° C above ambient) is undesirable, although required for operation at sub-ambient temperatures. From the standpoint of cost and safety, coolant injection presents the need for a valve, feed lines, and liquid $CO_2$ or $N_2$ holding tanks which are expensive and present obstacles to the operator. Also, temperature transients and gradients between different locations within the oven are relatively large when liquid coolant is used, resulting in a loss of chromatographic separation consistency.

SUMMARY OF THE INVENTION

In accordance with the illustrated embodiment, the present invention provides a gas chromatograph oven including a housing, and a door assembly having an external frame, and an internal, movable, spring mounted, oven closure hatch. The hatch has a first air passage therein and also establishes and closes a second air passage between the hatch and the housing. A movable, spring mounted cover opens and closes the first air passage in response to movement of the hatch. The door assembly also includes a front panel with a multiplicity of holes therein to allow the free-flow of air through the first air passage, and a plurality of air ducts to allow in the free-flow of air through the second air passage in the sides of this frame.

The invention permits room temperature air to flow into the oven with a reduction of turbulent interference between the hot air escaping from the oven and the ambient room air entering it. The internal movable hatch permits the escape of hot air at the edges of the oven interior and then through the air ducts in the door frame. Ambient room air is drawn into the oven interior through the first air passage which is fed by air entering the door assembly through the front panel. This arrangement separates the entering ambient air from the escaping hot air. Oven cooling above ambient room temperature is achieved without obstacles to the operator or exposed potentially hot surfaces, and without the use of auxiliary blowers or liquid $CO_2$ or $N_2$.

DESCRIPTION OF THE PREFERRED EMBODIMENT

Figure 1:
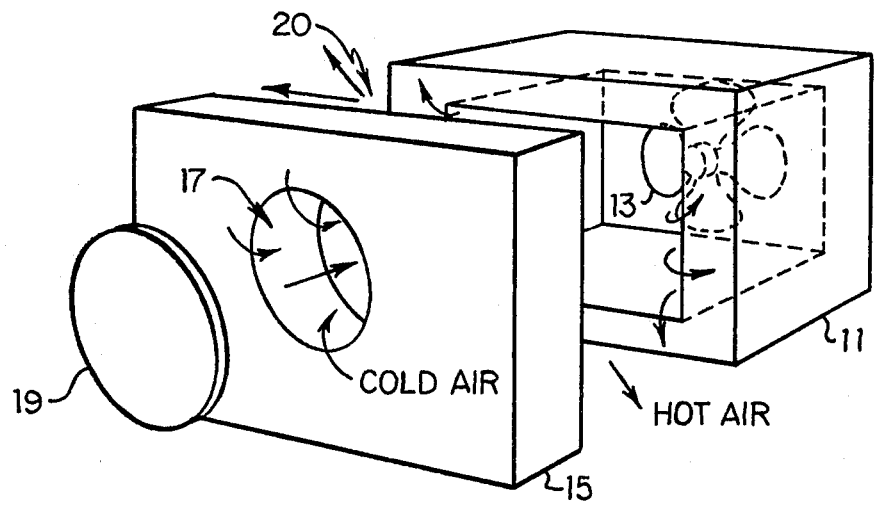
FIG. 1 is a perspective representation of some of the components used in one embodiment of the gas chromatograph oven of the present invention.

With reference to FIG. 1 there is shown a chromatograph oven housing 11 which is dimensioned to contain gas chromatograph separating columns, a heater (not shown), a motor driven stirring fan 13, and a thermally insulated hatch 15 defining a first air passage 17. Passage 17 may be closed with a cover 19. During operation at high temperatures on the order of 50° C–400° C, for example, hatch 15 is positioned directly over the opening of oven 11, thus closing it. Cover 19 closes off the first air passage 17. With hatch 15 sealing the opening of oven 11 and the first air passage 17 closed by cover 19, the oven operates in the conventional manner. In the cool-down mode of operation or during operation near ambient room temperature, the hatch 15 and cover 19 are in the relative positions shown in FIG. 1. Room air is drawn into the oven 11 through the first air passage 17 by the lower pressure region within the oven created by the rotating stirring fan 13. At the same time, the hot air within oven 11 is forced from the regions of greatest air pressure created by the stirring fan 13, through a second air passage 20 established by the space between the outer edge of the oven 11 and the hatch 15. This arrangement permits the lower pressure air region created within oven 11 to draw in ambient air and the higher pressure air region to exhaust hot air from the oven. The ambient air intake is positioned adjacent to the lower pressure region within oven 11 and the hot air exhaust is positioned adjacent to the higher pressure region.

Figure 2:
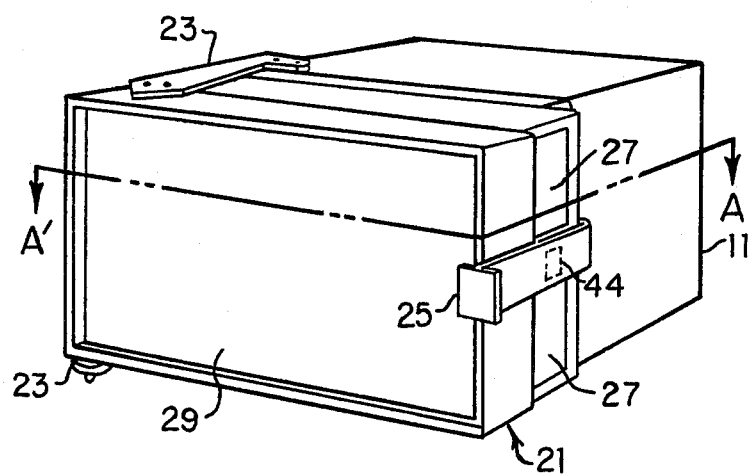
FIG. 2 is a perspective view of the exterior of one embodiment of a gas chromatograph oven incorporating the present invention.

FIG. 2 illustrates a chromatographic oven 11 with an oven door assembly 21 that internally contains a hatch 15 and a cover 19 in the configuration shown in FIG. 1. The oven door assembly 21 has a rigid exterior frame which is hinged to, and latches with, the main frame of the oven 11 by utilizing hinges 23 and the handle-latching mechanism 25. Also incorporated into door assembly 21 are air ducts 27 on each side of the door which cooperate with the second air passage 20. A front panel 29 with a multiplicity of holes therein allows the free-flow of air to the first air passage 17 in hatch 15. Door assembly 21 is so constructed that it is free to swing open as a complete unit when unlatched thus allowing access to the interior of the oven.

Figure 3:
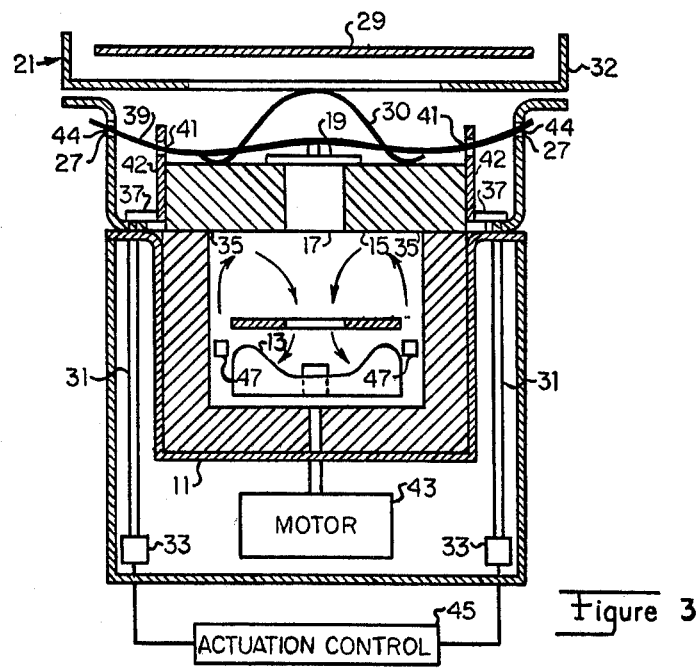
FIG. 3 is a cross-sectional view taken at the plane defined by lines A-A' in FIG. 2 with the internal oven hatch mechanism in a closed position.
Figure 4:
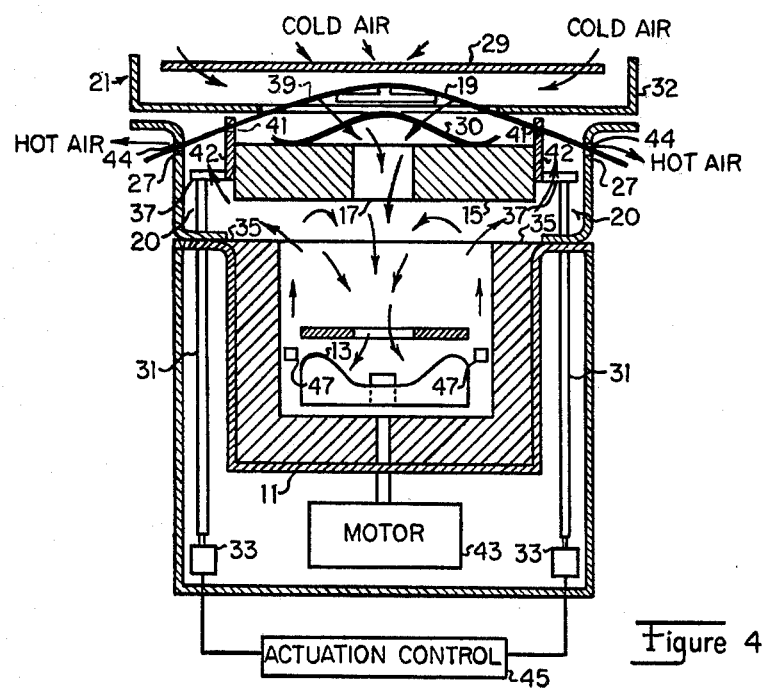
FIG. 4 is a cross-sectional view at the same plane as in FIG. 3 but with the internal oven hatch mechanism in an open position.

FIGS. 3 and 4 show the placement and interaction of the internal components of the oven door assembly 21 in more detail. In FIG. 3 the first air passage 17 and hatch 15 are closed, while in FIG. 4 the same elements are in an open configuration.

In operation, hatch 15 opens and closes oven 11 to permit cooling of its interior without necessitating the opening of the oven door assembly 21 on hinges 23. This is achieved by two mechanisms: a spring biasing mechanism 30 between hatch 15 and the exterior frame 32 of the door assembly 21; and a pair of push-rods 31 that open the hatch 15 under control of actuation devices 33. When the internal hatch 15 is closed, the spring biasing mechanism 30 applies the necessary bias force to maintain closure between the hatch 15 and the surface 35 which surrounds the opening of the oven 11. Hatch 15 opens when the actuation devices 33 are energized to impart a longitudinal motion to push-rods 31. Push-rods 31 extend through the rear of the exterior frame of the oven door assembly 21 and contact a pair of flanges 37 affixed to hatch 15 adjacent to the end of rods 31. When actuated, push-rods 31 open hatch 15 without opening the entire oven door assembly 21. Hatch 15 is held open against the bias of spring biasing mechanisms 30 as long as actuation devices 33 remain energized. When actuation devices 33 are deenergized, spring biasing mechanism 30 returns hatch 15 to the closed position.

More specifically, as shown in FIGS. 3 and 4, the first air passage cover 19 is attached to the center of a leaf spring 39. Each end of spring 39 passes through a first slot 41 in a frame 42 affixed to hatch 15, and a second slot 44 in the external frame of the oven door assembly 21. Slot 44 is also shown under latch 25 in dotted outline form in FIG. 2, between air ducts 27. Slots 41 and 44 are disposed slightly out of alignment so that the first air passage cover 19 is open and closed by the relative motion between hatch 15 and the external frame 32 of the oven door assembly 21. When hatch 15 is closed, the relative positions of slots 41 and 44 are such that leaf spring 39 holds cover 19 tightly closed over first air passage 17. When hatch 15 is opened by push-rods 31, the spring slots 41 and 44 change relative positions, thus bending the spring 39 in the opposite direction and causing the duct cover 19 to be withdrawn from first air passage 17.

The air flow within oven 11 is illustrated by the arrows in FIGS. 3 and 4. When hatch 15 and cover 19 are closed, as in FIG. 3, the stirring fan 13, circulates the air toward hatch 15 along the walls of the oven 11 and draws the returning air into the center of the fan 13. Air within the oven 11 is continuously mixed to achieve a uniform temperature throughout oven 11. When oven 11 is open for cooling, as depicted in FIG. 4, ambient air is drawn into the oven through the multiplicity of holes in the front door panel 29 and the first air passage 17. This air enters the center of the oven 11 as a result of the low pressure region created by the rotating stirring fan 13. The same rotational motion of the stirring fan 13 creates a higher pressure air region along the side walls of the oven. This causes some of the hot air to be exhausted through the second air passage 20 estabished around the edges of hatch 15 and through air ducts 27 in the oven door assembly 21. The remainder of the hot air is drawn into the center of the oven 11 and mixes with the ambient air entering through first air passage 17.

There is provided a hatch actuation control 45 which may be a programmable electronic circuit, for example. Actuation control 45 includes or interfaces with all of the necessary devices to control the temperature within the oven 11, e.g. fan motor 43, heater 47, and actuation devices 33. To cool oven 11 from a predetermined high temperature to a predetermined lower temperature, heater 47 is turned off. If sufficient cooling is not obtained by heat lost through the walls of oven 11 within a predetermined length of time, the actuation control 45 causes hatch 15 and cover 19 to open, thus opening first air passage 17 and establishing the second air passage 20 to provide ambient room temperature air for cooling. When the desired lower temperature is reached, heater 47 is again turned on. If heater 47 is unable to maintain the new lower temperature with continued cooling, the actuation control 45 would deenergize the actuation devices 33 and permit the bias force of spring 30 to close hatch 15 and cover 19. Since the walls of oven 11 do not cool as quickly as the air, the above cooling cycle would be repeated until temperature stabilization is achieved. Cyclic operation of the heater 47, and hatch 15 and cover 19 is also effective to achieve temperature stabilization if the oven temperature is being raised.

During venting, the oven heater 47 can be modulated on and off to control the temperature of the circulating oven air with acceptably small temperature transients and gradients in the chromatographic separation column region. The combination of the present invention and the modulated heater power allows chromatographic separations at temperatures as low as 5° C above ambient room temperature without the use of liquid $CO_2$ or $N_2$. The present invention also allows cooling of oven 11 from one temperature to a second temperature directly without substantially undershooting the second temperature. At relatively high second temperatures, the hatch 15 will be cycled by actuation control device 45 between venting and non-venting configurations until sufficient heat has been lost from the walls of oven 11. Thereafter hatch 15 remains in the non-venting configuration. The next chromatographic separation can begin as soon as the oven temperature is within the control range, although excessive residual oven wall heat may still be causing hatch 15 to cycle, thus saving time between chromatographic separations.

Figure 5:
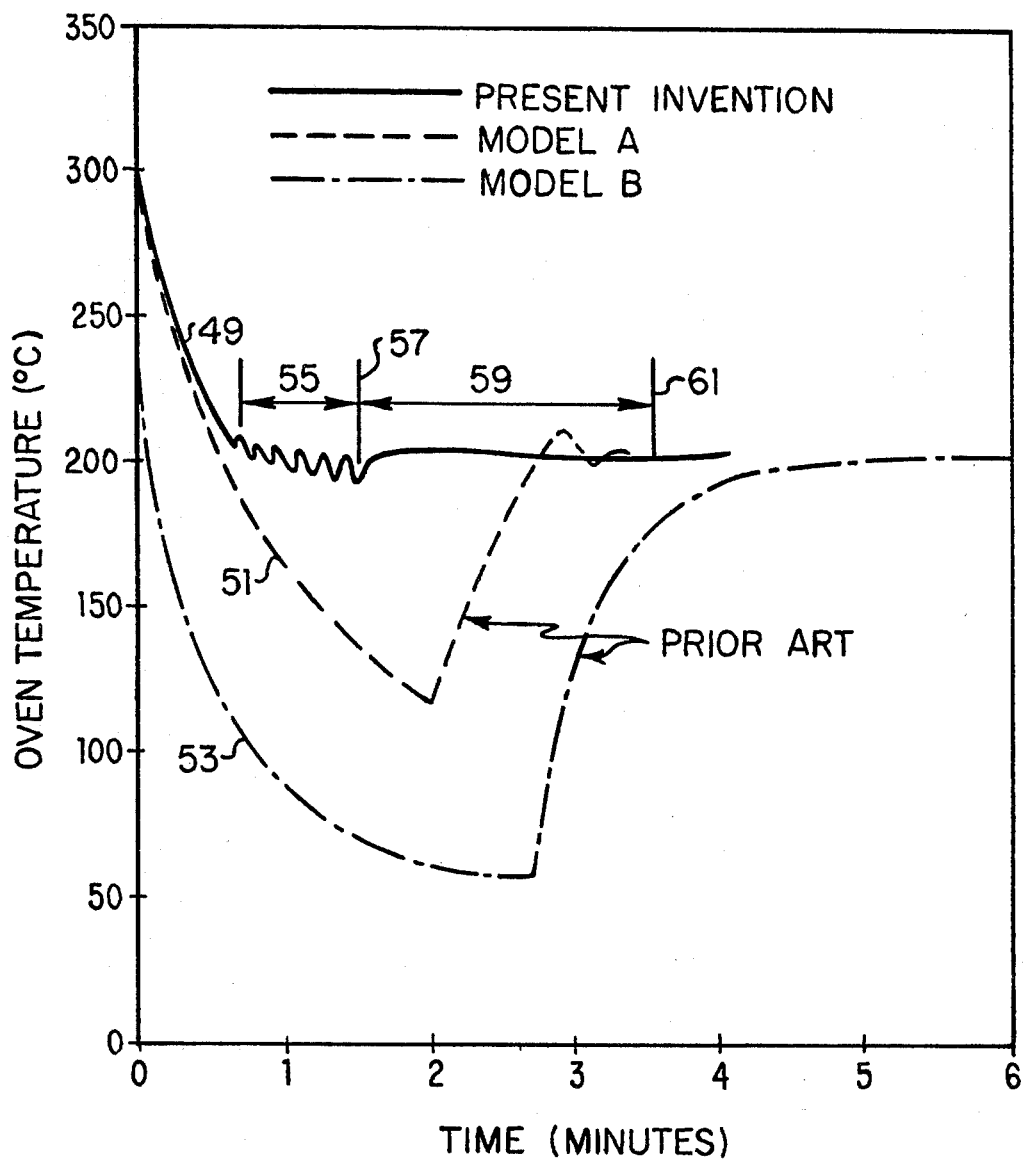
FIG. 5 is a plot of gas chromatograph oven temperature versus time that depicts a typical cooling cycle of three different gas chromatograph models including one utilizing the present invention.

FIG. 5 illustrates cooling of the chromatrograph oven 11 with the present invention by a curve 49. Curves 51 and 53 illustrate typical chromatograph oven cooling by two other chromatograph ovens. The temperature fluctuations depicted by curve 49 during a range of times 55 are a result of the opening and closing of hatch 15 when the oven 11 temperature is in the vicinity of the new temperature. Point in time 57 on curve 49 identifies the earliest time after which the oven temperature remains within the operational control temperature range for accurate chromatograph separation. Time range 59 on curve 49 represents an intentional 2 minute delay to allow the chromatograph separation columns to achieve temperature equilibrium, and time point 61 indicates the starting time for the next chromatograph separation.

I claim:

1. A gas chromatograph oven comprising:
   a thermally insulated housing having an oven door assembly closing one side thereof, one side of said housing defining a first air passage; p1 rotating stirring fan means for producing a high pressure region and a low pressure region within said housing;
   said oven door assembly including:
      a frame;
      a hatch;
      said hatch being movable into spaced-apart relation with said housing to define a second air passage;
      spring biasing means disposed between said hatch and said door frame to maintain closure of the housing open side by said hatch;
      cover means coupled with said hatch for selectively opening and closing said first air passage in response to the establishment and closure respectively, of said second air passage by movement of said hatch;
      actuation means for moving said hatch in opposition to said hatch spring biasing means, thereby to establish said second air passage and to open said first air passage;
   one of said first and second air passages being disposed adjacent said low pressure region to duct ambient room temperature air into said housing; and
   the other of said first and second air passages being disposed adjacent to said high pressure region to exhaust air from said housing.

2. A gas chromatograph oven as in claim 1 in which said oven door assembly spring biasing means comprises a partially compressed leaf spring attached to the oven door frame, said leaf spring being operable to apply a bias to said hatch toward closure of said housing.

3. A gas chromatograph oven as in claim 1 in which said actuation means comprises:
   a flange attached to said hatch;
   an actuation device providing rectilinear motion; and
   a push-rod means for communicating the rectilinear motion of the actuation device to the flange of said hatch in opposition to the bias force of the spring biasing means.

4. A gas chromatograph oven as in claim 1 wherein:
   said hatch further including means defining first and second mounting slots on opposite edges of the hatch, respectively;
   said oven door frame including means defining a mounting slot in close alignment with each of the slots in said hatch; and
   said cover means includes:
      a first air passage cover movably disposed adjacent to said first air passage;
      a snapping leaf spring, each end being disposed in one of said hatch mounting slots and the corresponding one of said door frame mounting slots, said leaf spring supporting said first air passage cover to maintain closure of the first air passage when the hatch is closed and to open said cover to a spaced-apart relation with the hatch by the motion of the hatch slots relative to the door frame slots.

5. A gas chromatograph oven as in claim 1 wherein said hatch defines a first air passage, and wherein said oven door assembly further comprises a front panel with a multiplicity of holes therein adjacent to said first air passage to allow the free-flow of air through the first air passage, said oven door frame further defining a plurality of air ducts adjacent to said second air passage to allow the free-flow of air through the second air passage, means for latching said oven door assembly to said housing, and means for pivotally hinging said oven door assembly onto the housing.

6. A gas chromatograph oven as in claim 1 in which said first air passage is disposed adjacent said low pressure region to duct ambient room temperature air into said housing, and said second air passage is disposed adjacent to said high pressure region to exhaust air from said housing.

7. A gas chromatograph oven as in claim 1 in which said second air passage is disposed adjacent said low pressure region to duct ambient room temperature air into said housing, and said first air passage is disposed adjacent to said high pressure region to exhaust air from said housing.

8. A gas chromatograph oven comprising:
   a thermally insulated housing having an oven door assembly engagable therewith for defining one side thereof, one side of said housing defining a first air passage; fans means disposed within said housing;
   said oven door assembly including:
      an external frame; and an internal oven closure hatch;
said hatch being movable independent of said frame into spaced-apart relation with said housing to define a second air passage;
cover means for selectively opening and closing said first air passage;
an actuation mechanism for opening said first air passage, and for moving said hatch to establish said second air passage;
one of said first and second air passages being operable to duct ambient room temperature air into said housing; and
the other of said first and second air passages being operable to exhaust air from said housing.

9. A gas chromatograph oven as in claim 8 wherein:
said oven door assembly further includes spring biasing means disposed between said hatch and said frame to maintain closure of said housing; and
said actuation mechanism includes:
first means coupled to said cover means for opening said first air passage; and
second means for moving said hatch in opposition to said biasing means for establishing said second air passage.

* * * * *

UNITED STATES PATENT AND TRADEMARK OFFICE
CERTIFICATE OF CORRECTION

PATENT NO. : 4,050,911
DATED : September 27, 1977
INVENTOR(S) : Paul Bryce Welsh It is certified that error appears in the above-identified patent and that said Letters Patent are hereby corrected as shown below:

Column 1, line 12, delete "colomns" and insert -- columns --;

Column 5, line 46, delete "pl";

Column 5, line 46, begin new paragraph with "rotating";

Column 6, line 66, delete "fans" and insert -- fan --.

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*